US006884870B2

(12) United States Patent
Hav et al.

(10) Patent No.: US 6,884,870 B2
(45) Date of Patent: Apr. 26, 2005

(54) FUSION PROTEINS FOR IDENTIFYING PROTEASES, PROTEASE TARGET SITES AND REGULATORS OF PROTEASE ACTIVITY IN LIVING CELLS

(75) Inventors: Bruce A. Hav, Pasadena, CA (US); Christine J. Hawkins, Park Orchards (AU)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/270,983

(22) Filed: Mar. 17, 1999

(65) Prior Publication Data

US 2002/0132327 A1 Sep. 19, 2002

Related U.S. Application Data

(60) Provisional application No. 60/078,721, filed on Mar. 20, 1998.

(51) Int. Cl.[7] ............................ C07K 14/00; C12P 21/04
(52) U.S. Cl. ........................ 530/350; 435/23; 435/24; 435/7.2; 435/7.21; 435/69.1; 435/69.2; 435/69.7; 536/23.4; 536/23.1; 536/23.2
(58) Field of Search ........................ 435/23, 24, 7.2, 435/7.21, 69.1, 69.2, 69.7; 536/23.4, 23.1, 23.2; 530/350

(56) References Cited

U.S. PATENT DOCUMENTS

| 5,599,906 | A | * | 2/1997 | Dasmahapatra | ............. 530/350 |
|---|---|---|---|---|---|
| 5,691,183 | A | | 11/1997 | Franzusoff et al. | ...... 435/252.3 |
| 5,716,622 | A | | 2/1998 | Darnell, Jr. et al. | ...... 424/185.1 |
| 5,830,462 | A | * | 11/1998 | Crabtree et al. | ......... 424/93.21 |
| 5,981,200 | A | * | 11/1999 | Tsien et al. | ................... 435/7.4 |
| 6,117,639 | A | * | 9/2000 | Germann et al. | ............... 435/6 |

OTHER PUBLICATIONS

Sakai et al., Sterol–regulated Release of SREBP–2 from Cell Membranes Requires Two Sequential Cleavages, One Within a Transmembrane Segment, Jun. 1996, Cell, vol. 85, pp 1037–1046.*
Knight et al. Fluorimetric Assays of Protelytic Enzymes, Methods in Enzymology 248: 18–34, 1995.*
Sarubbi et al., "A high throughput assay for inhibitors of HIV–1 protease," *FEBS*, 279(2):265–269 (1991).
Wearne, S. J., "Factor Xa cleavage of fusion proteins, Elimination of non–specific cleavage by reversible acylation," *FEBS*, 263(1):23–26 (1990).

* cited by examiner

Primary Examiner—Richard Hutson
(74) Attorney, Agent, or Firm—Gray Cary Ware & Freidenrich, LLP

(57) ABSTRACT

The invention provides a fusion protein including a reporter polypeptide, a linker polypeptide comprising a protease cleavage site, and a repressor polypeptide. The repressor polypeptide represses the activity of the reporter polypeptide by conferring a specific localization in a cell that reduces activity of the reporter activity until the cleavage site is cleaved. A method is also provided for identifying a protease that recognizes a specific protease cleavage site. The invention further provides a method of identifying a compound that activates a protease.

4 Claims, 3 Drawing Sheets

SEQUENCE LISTING

<160> NUMBER OF SEQ ID NOS: 12

<210> SEQ ID NO 1
<211> LENGTH: 10
<212> TYPE: PRT
<213> ORGANISM: Drosophila melanogaster

<400> SEQUENCE: 1

Glu Gln Lys Leu Ile Ser Glu Glu Asp Leu
1               5                   10

<210> SEQ ID NO 2
<211> LENGTH: 5
<212> TYPE: PRT

<213> ORGANISM: Simian virus 40

<400> SEQUENCE: 2

Lys Lys Lys Arg Lys
1               5

<210> SEQ ID NO 3
<211> LENGTH: 26
<212> TYPE: PRT
<213> ORGANISM: Artificial sequence
<220> FEATURE:
<223> OTHER INFORMATION: Product Synthesis, such as solid phase
      synthesis

<400> SEQUENCE: 3

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 4
<211> LENGTH: 30
<212> TYPE: PRT
<213> ORGANISM: Artificial sequence
<220> FEATURE:
<223> OTHER INFORMATION: Product Synthesis, such as solid phase
      synthesis

<400> SEQUENCE: 4

Asp Glu Val Asp Gly Trp Glu His Asp Gly Ile Glu His Asp Gly Ile
1               5                   10                  15

Glu Thr Asp Gly Asp Glu His Asp Gly Asp Gln Met Asp Gly
            20                  25                  30

<210> SEQ ID NO 5
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 5

Lys Asp Glu Leu
1

<210> SEQ ID NO 6
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 6

Trp Glu His Asp
1

<210> SEQ ID NO 7
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 7

Tyr Val Ala Asp
1

<210> SEQ ID NO 8
<211> LENGTH: 4
<212> TYPE: PRT
<213> ORGANISM: Artificial sequence
<220> FEATURE:
<223> OTHER INFORMATION: Product Synthesis, such as solid phase
      synthesis
<220> FEATURE:
<221> NAME/KEY: MISC_FEATURE
<222> LOCATION: (1)..(1)
<223> OTHER INFORMATION: Xaa is Trp or Leu

<400> SEQUENCE: 8

Xaa Glu His Asp
1

<210> SEQ ID NO 9
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 9

Asp Glu Val Asp
1

<210> SEQ ID NO 10
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 10

Val Glu Ile Asp
1

<210> SEQ ID NO 11
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 11

Leu Glu Thr Asp
1

<210> SEQ ID NO 12
<211> LENGTH: 4
<212> TYPE: PRT
<213> ORGANISM: Artificial sequence
<220> FEATURE:
<223> OTHER INFORMATION: Product Synthesis, such as solid phase
      synthesis

<400> SEQUENCE: 12

Leu Glu His Asp
1

FUSION PROTEINS FOR IDENTIFYING PROTEASES, PROTEASE TARGET SITES AND REGULATORS OF PROTEASE ACTIVITY IN LIVING CELLS

CROSS REFERENCE TO RELATED APPLICATIONS

This application claims priority from Provisional Application Ser. No. 60/078,721, filed Mar. 20, 1998, which is incorporated herein by reference its entirety and to which application a priority claim is made under 35 U.S.C. §119 (e).

FIELD OF THE INVENTION

This invention relates generally to the field of proteases, and specifically to polypeptides and methods useful in isolating proteases and assaying for protease inhibitors.

BACKGROUND OF THE INVENTION

Proteases are a class of enzymes, which play an important role in the processing of proteins. The body uses this mechanism to control several critical pathways or biochemical cascades, such as blood clot formation and complement activation. In neurons, specific proteases control pathways critical to neuronal communication and survival. Abnormal neuronal protease activity can lead to degenerative processes, as occurs during progressive disorders such as Alzheimer's disease and in phases of acute neuronal cell death resulting from head trauma and ischemia due to stroke. For example, these proteases can generate products that are neurotoxic, such as the amyloid beta protein ("Aβ") which forms the senile plaques seen in Alzheimer's disease patients, or initiate degradative cascades that are involved in breaking down the neuronal cytoskeleton, leading to nerve cell death.

The term "protease" is synonymous with "peptidase". Proteases comprise two groups of enzymes: the endopeptidases which cleave peptide bonds at points within the protein, and the exopeptidases, which remove amino acids sequentially from either N or C-terminus respectively. The term proteinase is also used as a synonym for endopeptidase. The four mechanistic classes of proteinases are: serine proteinases, cysteine proteinases, aspartic proteinases, and metallo proteinases. In addition to these four mechanistic classes, there is a section of the enzyme nomenclature which is allocated for proteases of unidentified catalytic mechanism. This indicates that the catalytic mechanism has not been identified. Thus, the possibility remains that novel types of proteases do exist.

The serine proteinases include two distinct families. The chymotrypsin family which includes the mammalian enzymes such as chymotrypsin, trypsin or elastase or kallikrein and the substilisin family which includes the bacterial enzymes such as subtilisin. The general 3D structure is different in the two families but they have the same active site geometry and then catalysis proceeds via the same mechanism. The serine proteinases exhibit different substrate specificities which are related to amino acid substitutions in the various enzyme subsites interacting with the substrate residues. Some enzymes have an extended interaction site with the substrate whereas others have a specificity restricted to the P1 substrate residue. Three residues which form the catalytic triad are essential in the catalytic process i.e His 57, Asp 102 and Ser 195 (chymotrypsinogen numbering). The first step in the catalysis is the formation of an acyl enzyme intermediate between the substrate and the essential serine. Formation of this covalent intermediate proceeds through a negatively charged tetrahedral transition state intermediate and then the peptide bond is cleaved. During the second step or deacylation, the acyl-enzyme intermediate is hydrolyzed by a water molecule to release the peptide and to restore the Ser-hydroxyl of the enzyme. The deacylation which also involves the formation of a tetrahedral transition state intermediate, proceeds through the reverse reaction pathway of acylation. A water molecule is the attacking nucleophile instead of the Ser residue. The His residue provides a general base and accept the OH group of the reactive Ser.

The cysteine proteinases includes the plant proteases such as papain, actinidin or bromelain, several mammalian lysosomal cathepsins, the cytosolic calpains (calcium-activated) as well as several parasitic proteases (e.g Trypanosoma, Schistosoma). Papain is the archetype and the best studied member of the family. Recent elucidation of the X-ray structure of the Interleukin-1-beta Converting Enzyme has revealed a novel type of fold for cysteine proteinases. Like the serine proteinases, catalysis proceeds through the formation of a covalent intermediate and involves a cysteine and a histidine residue. The essential Cys25 and His 159 (papain numbering) play the same role as Ser195 and His57 respectively. The nucleophile is a thiolate ion rather than a hydroxyl group. The thiolate ion is stabilized through the formation of an ion pair with neighboring imidazolium group of His159. The attacking nucleophile is the thiolate-imidazolium ion pair in both steps and then a water molecule is not required.

Most of aspartic proteinases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteinases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme. In contrast to serine and cysteine proteases, catalysis by aspartic proteinases do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO-NH bond cleavage. This general acid-base catalysis, which may be called a "push-pull" mechanism leads to the formation of a noncovalent neutral tetrahedral intermediate.

The metallo proteinases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain a specific sequence which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a noncovalent tetrahedral intermediate after the attack of a zinc-bound water molecule on the carbonyl group of the scissile bond. This intermediate is further decomposed by transfer of the glutamic acid proton to the leaving group.

Studies in a number of organisms has shown that cell death is under genetic control, and that components that regulate cell survival and death are evolutionarliy conserved, indicating that a universal cell death program exists in multicellular organisms. Apoptosis was recognized as death by an orchestrated sequence of cuts performed by enzymes which degrade macromolecular structures like DNA. A central step in carrying out cell death is the activation of members of a family of cysteine-dependent-specific proteases, now known as caspases (Nicholson and Thomberry, *TIBS* 22:299, 1997, herein incorporated by reference). Caspases are cysteine proteases bearing an active site with a conserved amino acid sequence and which cleave specifically following aspartate residues. These proteases were dubbed caspase as they are cysteine dependent) and caspartate cleaving protease. Caspases sufficient to carry out cell death can be expressed ubiquitously, indicating that their activation and activity must be tightly controlled in normal cells (Weil, M., et al., *J Cell Biol.* 133:1053, 1996). Caspase-1 (formerly called ICE, interleukin 1b-converting enzyme) was the first member of the caspase family to be identified as a protease involved in mammalian apoptosis because of its homology with CED-3. The latter gene product was known for its requirement in the execution of apoptosis in the nematode *C. elegans* (Yuan, et al., *Cell* 75:641–652, 1993). To date ten mammalian members of this family have been identified by structure and substrate specificity. There is also evidence that caspases may play roles in processes other than cell death (e.g., Song et al., *Science* 275:536, 1997).

Viral and cellular activators and inhibitors of protease activation or activity have been identified (e.g., Nicholson and Thomberry, supra). For caspase, many of these proteins were initially identified as regulators of apoptosis, and were subsequently tested for their ability to regulate caspase function. The present invention provides a novel fusion polypeptides and methods useful in the isolation of proteases, and in the identification of protease inhibitors.

SUMMARY OF THE INVENTION

The invention provides polypeptides and methods useful in isolating proteases and assays for protease inhibitors.

Ina first embodiment, the invention provides a fusion protein including a reporter polypeptide linked to a linker polypeptide comprising a protease cleavage site, and a repressor polypeptide that represses the activity of the reporter polypeptide. The repressor polypeptide is operatively linked to the linker polypeptide. Cleavage of the linker polypeptide at the protease cleavage site increases the activity of said reporter.

A method is also provided for identifying a protease that recognizes a specific protease cleavage site. The method includes providing a cell comprising a fusion protein including a reporter polypeptide linked to a linker polypeptide comprising a protease cleavage site, and a repressor polypeptide that represses the activity of said reporter polypeptide. The repressor polypeptide is operatively linked to the linker polypeptide, and cleavage of the linker polypeptide at the protease cleavage site increases the activity of said reporter polypeptide. A test protease is expressed in the cell, the activity of the reporter in the cell is compared with the activity of the reporter in a cell not expressing said test protease. In this method an increased activity of the reporter indicates cleavage of the protease cleavage site by the test protease.

The invention further provides a method of identifying a compound that inhibits a protease. The method includes providing a cell including a fusion protein of a reporter polypeptide linked to a linker polypeptide with a protease cleavage site, and a repressor polypeptide that represses the activity of the reporter. The repressor polypeptide is operatively linked to the linker polypeptide such that cleavage of the linker polypeptide at the protease cleavage site increases the activity of said reporter polypeptide. A protease that cleaves at the protease cleavage site is also provided. The cell is contacted with the compound under conditions sufficient for said components to interact, and the activity of the reporter is measured. A decrease in the activity of the reporter indicates an ability of the compound to inhibit the protease.

The invention further provides a method of identifying a compound that activates a protease The method includes providing a cell including a fusion protein of a reporter polypeptide linked to a linker polypeptide with a protease cleavage site, and a repressor polypeptide that represses the activity of the reporter. The repressor polypeptide is operatively linked to the linker polypeptide such that cleavage of the linker polypeptide at the protease cleavage site increases the activity of said reporter polypeptide. A protease that cleaves at the protease cleavage site is also provided. The cell is contacted with the compound under conditions sufficient for said components to interact, and the activity of the reporter is measured. A increase in the activity of the reporter indicates an ability of the compound to activate the protease.

BRIEF DESCRIPTION OF THE DRAWINGS

FIG. 3 is a graph illustrating that the expression of caspase inhibitors suppresses caspase-dependent reporter activation in yeast. The LexAβ-gal reporter strain carrying pGALL-CLBDG6 was transformed with either an empty pCUP1 plasmid or pCUP1-CED-3, and either an empty pGALL vector or pGALL-p35. Three colonies from each transformation were grown for 24 hours in selective gal/raf medium. Cultures were diluted 1:10 into fresh gal/raf medium containing 3 µM copper sulfate, grown for a further 10 hours, after which ONPG assays for β-gal activity were performed.

FIG. 4 is two graphs plotting the time course of the release of AFC over time.

DESCRIPTION OF THE PREFERRED EMBODIMENTS

Figure 1B:
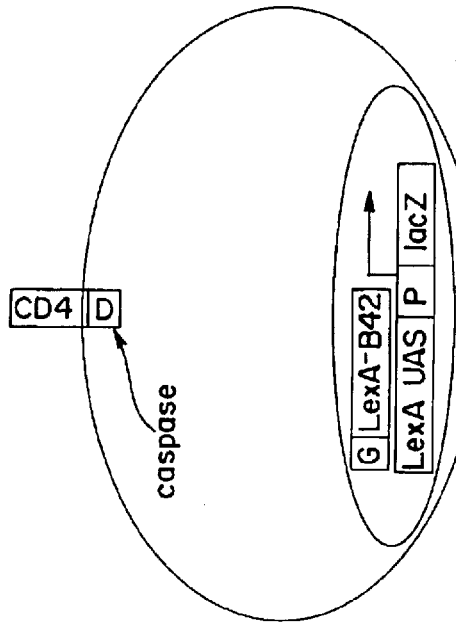
FIG. 1 is a schematic diagram illustrating a genetic system for monitoring caspase activity in yeast using a transcriptional reporter. Yeast were created that express a chimeric type-1 transmembrane protein (CLBDG6) in which the N-terminal signal sequence and transmembrane domain (CD4) is followed by a linker consisting of 6 tetrapeptide caspase target sites (indicated in bold) that bracket the specificity of known caspases and granzyme B (Thornberry, N. A., et al., *J. Biol. Chem.* 272: 17907–17911, 1997)- DEVDG-WEHDG-IEHDG-IETDG-DEHDG-DQMDG— (SEQ ID NO:4) each of which is followed by a glycine residue, which acts as a stabilizing residue in the N-end rule degradation pathway in yeast (reviewed in Varshavsky, A., *Proc. Natl. Acad. Sci. USA* 93: 12142–12149, 1996). C-terminal to the caspase target site linker is a transcription factor domain, LexA-B42. The LexA-dependent transcriptional reporter consists of LexA binding sites (LexA UAS) and a promoter (P) upstream of the bacterial lacZ gene (lacZ) (FIG. 1A). The cells in FIG. 1A act as caspase activity reporters since expression of an active caspase results in CLBDG6 cleavage at the caspase target sites, releasing LexA-B42, which enters the nucleus and activates lacZ transcription (see FIG. 1B). A version of CLBDG6 in which the P1 aspartates are changed to glycines (CLBGG6) cannot be cleaved by caspases. Cells expressing CLBGG6 act as false positive reporters for molecules that activate lacZ expression independent of cleavage at caspase target site (FIG. 1C).
As shown in FIG. 1D, if the cells in shown in FIG. 1B express a caspase inhibitor as well as an active caspase, caspase activity, and thus caspase-dependent release of LexA-B42, is inhibited. β-gal levels are decreased compared to cells that express the caspase alone.

The invention provides a fusion protein useful for detecting and characterizing proteases and for identifying protease inhibitors. The fusion proteins of the invention include: (1) a reporter polypeptide (2) a linker polypeptide comprising a protease cleavage site, and (3) a repressor polypeptide. Cleavage of the linker polypeptide at the protease cleavage site increases the activity of the reporter.

It should be noted that as used herein and in the appended claims, the singular forms "a," "and," and "the" include plural referents unless the context clearly dictates otherwise. Thus, for example, reference to "a polypeptide" includes a plurality of such polypeptides and reference to "the compound" includes reference to one or more compounds and equivalents thereof known to those skilled in the art, and so forth.

Unless defined otherwise, all technical and scientific terms used herein have the same meaning as commonly understood to one of ordinary skill in the art to which this invention belongs. Although any polypeptides, compounds and materials similar or equivalent to those described herein can be used in the practice or testing of the invention, the preferred methods, devices and materials are now described.

All publications mentioned herein are incorporated herein by reference in full for the purpose of describing and disclosing the cell lines, polypeptides and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Polypeptides and Polynucleotides

As used in connection with the present invention the term "polypeptide" or "protein" refers to a polymer in which the monomers are amino acid residues which are joined together through amide bonds. When the amino acids are alpha-amino acids, either the L-optical isomer or the D-optical isomer can be used, the L-isomers being preferred. The term "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein. "Substantially the same" means that an amino acid sequence is largely, but not entirely, the same, but retains a functional activity of the sequence to which it is related. In general two amino acid sequences are substantially the same" or "substantially homologous" if they are at least 85% identical. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

A "reporter" polypeptide is any polypeptide whose presence in a sample may be assayed. The assay may be a chemical reaction such as an enzymatic assay or a physical detection such as spectrophotometric detection of a reaction product. In one specific, nonlimiting example, the reporter polypeptide can be an enzyme, such as β-glucuronidase (GUS), luciferase, chloramphenicol transacetylase (CAT), and β-galactosidase. The enzyme can be a kinase, such that removal of an inhibitory domain releases the catalytic domain. The presence of the active kinase can then be detected by phosphorylation of a substrate. The activity of the enzyme or presence of reaction products can then be detected. Many assays and detection schemes well known to one of skill in the art for various reporter polypeptides can be utilized with the subject invention.

In another nonlimiting example, the reporter polypeptide can be a fluorescent molecule. On example of such a fluorescent molecule is a green fluorescent proteins (e.g., Aequorea victoria, Renilla reniformis, and Phialidium gregarium green fluorescent proteins; see, Ward, W. W., et al., Photochem. Photobiol. 35:803–808, 1982; and Levine, L. D., et al., Comp. Biochem. Physiol., 72B:77–85, 1982). Two proteins, wherein a fluorescence energy transfer occurs between the two proteins, can also be used as a reporter polypeptide. In one embodiment, the two proteins are linked by a protease cleavage site, such that a different emission spectra is seen when the two fluorescent polypeptides are attached and when they are separated.

In yet another nonlimiting example, the reporter polypeptide contains an epitope that can be bound by an antibody. A labeled form of the antibody, or a secondary antibody that binds the antibody that in turn binds the reporter polypeptide, can then be used to assay the presence of the antibody. One of skill in the art can readily determine a detection scheme useful for visualizing an immunologic epitope with a specific antibody.

In one embodiment, the reporter polypeptide is a transcriptional activator. A "transcriptional activator" is a polypeptide that increases the transcription of a nucleic acid as compared to transcription in the absence of the transcriptional activator. In one nonlimiting example, the transcriptional activator is LEXA-B42. The presence of the transcriptional activator is detected utilizing an assay system including a nucleic acid containing a binding site for the transcriptional activator and a nucleic acid encoding a second reporter polypeptide. The presence of the second reporter is then detected using methods known in the art such as those described above. In a nonlimiting example, the second reporter polypeptide is an enzyme, (e.g., β-glucuronidase (GUS), luciferase, chloramphenicol transacetylase (CAT), and β-galactosidase). In another nonlimiting example, the second reporter is involved in cell death. The second reporter can be toxic to the cell. Upon activation by the transcriptional activator, the second reporter is produced, and cell death results. One polypeptide which can be used as a reporter is the URA3, which confers expression-dependent toxicity. Yeast cells that express the URA3 gene grow on media lacking uracil, and yeast cells lacking URA3 can grow only if supplied with uracil in the surrounding media. The URA3 gene catalyzes the transformation of 5-fluoroortic acid (FOA) into a toxic compound (Lam et al., EMBO J. 12:2705, 1993). Yeast that are deficient in URA3 grow on a media containing uracil and FOA survive, but die if expression of the URA3 gene is induced. Cells that carry a construct containing a binding site for a transcriptional activator operatively linked to a nucleic acid encoding URA3 are thus sensitive to the presence of the transcriptional activator that binds to the binding site.

The reporter polypeptide is attached to a repressor domain that renders the protein nonfunctional. Upon cleavage by a protease in the linker domain (see below), the enzyme becomes active. A "linker polypeptide" refers to a polypeptide containing a protease cleavage site; cleavage at this site results in the ability to detect the reporter polypeptide. Thus, the reporter polypeptide can be detected once it is separated from a repressor polypeptide (see below) by cleavage at the linker polypeptide. It should be noted that the linker polypeptide can be a synthetic polypeptide containing a protease cleavage site. Alternatively, the linker polypeptide can be an integral part of, and therefore included in, the reporter polypeptide or the repressor polypeptide, so long as cleavage at this site results in removal of the repressor from the reporter polypeptide. Cleavage of the linker polypeptide at the protease cleavage site results in an increased ability to detect the reporter polypeptide. When two polypeptides, such as a linker polypeptide and a reporter polypeptide, are "linked" they are joined. In this manner one polypeptide is joined to a second polypeptide through amide bonds.

In one embodiment, the linker polypeptide includes a caspase cleavage site. The caspases cleave their substrates after an Aspartate in a recognition sequence of four amino acids with the conserved Aspartate at position S1 and variability in positions S4–S2 (XXXD). On the basis of the recognition sequence the caspase family can be subdivided into three groups (see Table 1 below).

TABLE 1

Characteristics of the Caspase Family

| Group | Caspase | Synonym | S4-S1 recognition sequence (4 amino acids) | Substrate |
|---|---|---|---|---|
| Group 1 | caspase-1 | ICE | WEHD (SEQ ID NO:6), YVAD (SEQ ID NO:7) | Pro-IL1B, pro-caspases-1,-3,14 |
| | caspase-4 | ICErel-II, TX, ICH-2 | (W/L)EHD (SEQ ID ID NO:8) | Pro-IL1B, procaspase-1 |
| | caspase-5 | ICErel-II, TY | (W/L)EHD (SEQ ID NO:8) | unknown |
| Group 2 | caspase-3 | CPP32, Yama, apopain | DEVD (SEQ ID NO:9) | PARP, DFF, SREBP, rho-GD1, pro-caspase-6,-9 |
| | caspase-2 | ICH-1 | | PARP |
| | caspase-7 | Mch3, ICE-LAP3, CMH-1 | DEVD (SEQ ID NO:9) | PARP, pro-caspase-6 |
| Group 3 | caspase-6 | Mch2 | VEID (SEQ ID NO:10) | Lamins A, B1/B2, C, PARP |
| | caspase-8 | FLICE, MAC, Mch5 | LETD (SEQ ID NO:11) | PARP |
| | caspase-9 | ICE-LAP6, Mch6 | LEHD (SEQ ID NO:12) | PARP |
| | caspase-10 | Mch4 | | Procaspases-3,-7 |

A "repressor" polypeptide is a polypeptide that is capable of inhibiting or reducing the activity or inhibiting the ability to detect a reporter polypeptide to which it is bound. The repressor may interact directly with the reporter polypeptide to repress its activity or function. Alternatively, the repressor may confer a specific localization in the cell such that the reporter has reduced activity. In one embodiment, the repressor is a transmembrane polypeptide.

In one embodiment, the reporter is a transcriptional activator and the repressor is a nuclear export sequence. A "nuclear export sequence" is a polypeptide sequence that directs the polypeptide to a region of a cell outside of the nucleus. When the repressor and the reporter polypeptides are connected by the linker polypeptide the polypeptides are transported out of the nucleus; the transcriptional activator will not activate transcription. In one embodiment, the repressor is a transmembrane polypeptide, and the reporter is a transcriptional activator; the transcriptional activator is linked to the transmembrane polypeptide by a linker including a protease cleavage site attached to the intracellular domain of the transmembrane protein. Following cleavage of the linker polypeptide, the transcriptional activator released from the membrane localization. Thus, transcriptional activation by the reporter occurs following removal of the repressor polypeptide.

In one nonlimiting example the repressor is CD4, which transports a polypeptide outside of the nucleus of a cell. In a second, specific, nonlimiting example, the repressor is amyloid precursor protein, which transports a polypeptide outside of the nucleus of a cell.

In the case of eukaryotes, the repressor may be a signal peptide. A signal peptide is believed to function to transport the fusion polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties to those described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting," Chapter 35, of Stryer, L., *Biochemistry*, 4th ed., W. H. Freeman, 1995. The localization sequence can also be a localized protein. Some important localization sequences include those targeting the nucleus (KKKRK) (SEQ ID NO: 2), mitochondrion (amino terminal MLRTSSLFTRRVQPSLFRNILRLQST-) (SEQ ID NO: 3), endoplasmic reticulum (KDEL (SEQ ID NO:5) at C-terminus, assuming a signal sequence present at N-terminus), peroxisome (SKF at C-terminus), prenylation or insertion into plasma membrane (CaaX, CC, CXC, or CCXX at C-terminus), cytoplasmic side of plasma membrane (fusion to SNAP-25), or the Golgi apparatus (fusion to furin).

Nucleic Acids

In another embodiment, the invention provides isolated nucleic acid sequences which encode the polypeptides of the invention.

"Polynucleotide" or "nucleic acid sequence" refers to a polymeric form of nucleotides at least 10 bases in length. By isolated nucleic acid sequence" is meant a polynucleotide that is not immediately contiguous with both of the coding sequence with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

Nucleic acid sequences which encode a fusion protein of the invention can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequences encoding the fusion protein of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; tobacco mosaic virus, TMV. The nucleic acid sequences encoding a fusion polypeptide of the invention can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., 1989, and *Current Protocols in Molecular Biology*, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., *Methods in Enzymology* 153:516–544, 1987). These elements are well known to one of skill in the art.

In yeast, a number of vectors containing constitutive or inducible promoters may be used. For a review see, *Current Protocols in Molecular Biology*, Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology*, Eds. Wu & Grossman, 1987, Acad. Press, N.Y., Vol. 153, pp. 516–544, 1987; Glover, *DNA Cloning*, Vol. II, IRL Press, Wash., D.C., Ch. 3, 1986; and Bitter, "Heterologous Gene Expression in Yeast," *Methods in Enzymology*, Eds. Berger & Kimmel, Acad. Press, N.Y., Vol. 152, pp. 673–684, 1987; and *The Molecular Biology of the Yeast Saccharomyces*, Eds. Strathem et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: *DNA Cloning Vol. 11, A Practical Approach*, Ed. DM Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

By "transformation" is meant a permanent genetic change induce in a cell following incorporation of new DNA (i.e., DNA exogenous to the cell). Where the cell is a mammalian cell, the permanent genetic change is generally achieved by introduction of the DNA into the genome of the cell.

By "transformed cell" is meant a cell into which (or into an ancestor of which has been introduced, by means of recombinant DNA techniques, a DNA molecule encoding a fusion protein consisting of an optical sensor operatively fused to a responsive polypeptide, or fragment thereof, which normally has two or more conformational shapes, and which undergoes a conformational change during a cell signaling event.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukarotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell. In one embodiment, the mammalian cell is a human cell.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38. In one embodiment, the eukaryotic cell is a human cell.

Mammalian cell systems which utilize recombinant viruses or viral elements to direct expression may be engineered. For example, when using adenovirus expression vectors, the nucleic acid sequences encoding a fusion protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, *Proc. Natl. Acad. Sci. USA*, 81:3655–3659, 1984). Alternatively, the vaccinia virus 7.5K promoter may be used. (e.g., see, Mackett, et al., *Proc. Natl. Acad. Sci. USA*, 79:7415–7419, 1982; Mackett, et al., *J. Virol.* 49:857–864, 1984; Panicali, et al., *Proc. Natl. Acad. Sci. USA* 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, *Proc. Natl. Acad. Sci. USA*, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Proc. Natl. Acad. Sci. USA*, 77:3567, 1980; O'Hare, et al., *Proc. Natl. Acad Sci. USA*, 8:1527, 1981); gpt, which confers resistance to mycophenolic acid (Mulligan & Berg, *Proc. Natl. Acad. Sci. USA*, 78:2072, 1981; neo, which confers resistance to the aminoglycoside G-418 (Colberre-Garapin, et al, *J. Mol. Biol* 150:1, 1981); and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-arnithine, DFMO (McConlogue L., In: *Current Communications in Molecular Biology*, Cold Spring Harbor Laboratory, ed., 1987).

A fusion protein of the invention can be produced by expression of nucleic acid encoding the protein in prokaryotes. These include but are not limited to microorganisms such as bacteria transformed with recombinant bacteriophage DNA, plasmid DNA or cosmid DNA expression vectors encoding a fusion protein of the invention. A primary advantage of the fusion proteins of the invention is that they are prepared by normal protein biosynthesis, thus completely avoiding organic synthesis and the requirement for customized unnatural amino acid analogs. The constructs can also be expressed in *E. coli* in large scale. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. The fusion proteins of the invention can also be engineered to contain a cleavage site to aid in protein recovery.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

Screening Assays

The invention also provides a method for determining the presence of an activity in a sample, a protease that recognizes a specific protease cleavage site. The method includes providing a cell comprising a fusion protein comprising a reporter polypeptide linked to a linker domain comprising a protease cleavage site and a repressor domain that represses the activity of the reporter. The repressor domain is operatively linked to the linker domain, such that cleavage of the linker domain at the protease cleavage site increases the activity of said reporter. This fusion polypeptide is expressed in a cell in addition to expressing a test protease in the cell. The activity of the reporter in the cell expressing the test protease is then compared with the expression of the reporter in a cell not expressing the test protease. In this system, an increased activity of the reporter indicates cleavage of the protease cleavage site by the test protease. The cell may be a prokaryotic or a eukaryotic cell. In one embodiment, the cell is a yeast cell. In another embodiment, the cell is a mammalian cell such as a human cell.

In one embodiment, the cell does not naturally express the protease. The test protease is therefore transfected as a separate construct into the cell, so that the cell is transformed with two nucleic acids: one encoding the test protease and one encoding the fusion polypeptide of the invention.

In another embodiment, the fusion protein of the invention is expressed in a cell naturally expressing a test protease. The activity of the reporter is then compared to the activity of a control cell that expresses the fusion protein of the invention, but does not expressing the test protease. Techniques well known to one of skill in the art (e.g., subtractive hybridization) can then be used to isolate the test protease. In a further embodiment, the invention features a method for determining if a cell exhibits a protease activity, which includes the steps of:

(1) transfecting the cell with a nucleic acid encoding a fusion protein of the invention,
(2) measuring the activity of the reporter polypeptide. The activity of the reporter polypeptide can be compared to a suitable control.

The invention can be used in screening assays to determine whether a compound alters the activity of a particular polypeptide, such as a protease. In one embodiment, the assay is performed on a sample of cells cultured in vitro containing a fusion protein of the invention. In the method of the invention a cell is provided including a fusion protein comprising a reporter polypeptide linked to a linker domain including a protease cleavage site and a repressor domain that represses the activity of said reporter. The repressor domain is operatively linked to the linker domain. Cleavage of the linker domain at the protease cleavage site increases the activity of said reporter. The cell also includes a protease that cleaves at the protease cleavage site. The cell is then contacted with a compound under conditions sufficient for the components to interact. The activity of the reporter is then measured.

"Altering" refers to an increase or a decrease in the activity of a protein such as a protease. A decrease in the activity of the reporter indicates an ability of the compound to inhibit the protease. An increase in the activity of the reporter indicates an ability of the compound to activate the protease. In general a "decrease" is a reduction in the activity or expression of the reporter by at least 30% as compared to a control cell, not contacted with the compound. In one embodiment, the decrease is two-fold or more. Similarly, an "increase" is a induction of the activity or expression of the reporter by at least 30% as compared to a control cell, not contacted with the compound. In one embodiment, the increase is two-fold or more.

The term "compound" denotes derivatives antibodies, peptides, chemical compounds or pharmaceuticals that affect an activity of a protease of interest. "Incubating" includes conditions which allow contact between the test composition and the protease. Contacting includes in solution and in solid phase.

The test ligand(s)/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237, 1988).

Any of a variety of procedures may be used to clone the genes of use with the method of the present invention when the test composition is in a combinatorial library or is expressed as a gene product (as opposed to a chemical composition). One such method entails analyzing a shuttle vector library of DNA inserts (derived from a cell which expresses the composition) for the presence of an insert which contains the composition gene. Such an analysis may be conducted by transfecting cells with the vector and then assaying for expression of the composition binding activity. The preferred method for cloning these genes entails determining the amino acid sequence of the composition protein. Usually this task will be accomplished by purifying the desired composition protein and analyzing it with automated sequencers. Alternatively, each protein may be fragmented as with cyanogen bromide, or with proteases such as papain, chymotrypsin or trypsin (Oike, Y., et al., J. Biol. Chem., 257:9751–9758, 1982; Liu, C., et al., Int. J. Pept. Protein Res., 21:209–215, 1983). Although it is possible to determine the entire amino acid sequence of these proteins, it is preferable to determine the sequence of peptide fragments of these molecules.

The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that affects an activity of a protease.

In one embodiment the compound inhibits the activity of the protease, and is an antibody, or a biologically active fragment thereof, which interferes binds to a protease of interest. A protease can be used to produce antibodies which are immunoreactive or bind to epitopes of the protease. Antibodies which consist essentially of pooled monoclonal antibodies with different epitopic specificities, as well as distinct monoclonal antibody preparations are included.

Polyclonal antibodies can also be used in the method of the invention. The preparation of polyclonal antibodies is well-known to those skilled in the art. See, for example, Green et al, "Production of Polyclonal Antisera," in: Immunochemical Protocols, pages 1–5, Manson, ed., Humana Press, 1992; Coligan et al, "Production of Polyclonal Antisera in Rabbits, Rats, Mice and Hamsters," in: Current Protocols in Immunology, section 2.4.1, 1992, which are hereby incorporated by reference.

The preparation of additional monoclonal antibodies likewise is conventional. See, for example, Kohler & Milstein, Nature 256:495, 1975; Coligan et al., sections 2.5.1–2.6.7; and Harlow et al., in: Antibodies: a Laboratory Manual, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)," in: Methods in Molecular Biology, Vol. 10, pages 79–104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growthsustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies of the present invention may also be derived from subhuman primate antibody. General techniques for raising therapeutically useful antibodies in baboons can be found, for example, in Goldenberg et al., International Patent Publication WO 91/11465, 1991, and Losman et al., *Int. J. Cancer* 46:310, 1990, which are hereby incorporated by reference.

Alternatively, an antibody that binds a protease may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

Antibodies of the invention also may be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994, which are hereby incorporated by reference.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and No. 4,331,647, and references contained therein. These patents are hereby incorporated in their entireties by reference. See also Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: a Companion to Methods in Enzymology*, Vol. 2, page 97, 1991; Bird et al., *Science* 242:423–426, 1988; Ladner et al., U.S. Pat. No. 4,946,778; Pack et al., *Bio/Technology* 11:1271–77, 1993; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106, 1991.

Antibodies can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991, incorporated by reference).

The monoclonal antibody which binds a protease or a biologically active fragment thereof can be utilized alone, or in combination with another agent.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Materials and Methods

Yeast Strains.

The W303α strain (MATα, can1-100, leu2-3,-112, his3-11,-15, trp1-1, ura3-1, ade2-1) was used to monitor caspase activity using the lacZ reporter system. EGY48 (MATa, ura3, trp1, his3, LexAop$_6$-LEU2) (Invitrogen) was used to monitor caspase-dependent cell killing.

Construction of Caspase Target Site Fusion Proteins.

The reporter, CLBDG6, was generated using PCR and standard techniques (details provided on request). This protein consists of, from N- to C-terminus, amino acids 1–401 of a type 1 transmembrane protein, human CD4 (Madden, P. J., et al., *Cell* 42:93–104, 1985), a linker consisting of 6 tetrapeptide caspase target sites that bracket the specificity of known caspases and granzyme B (Thornberry, N. A., et al., *J. Biol. Chem.* 272:17907–17911, 1997)-DEVDG-WEHDG-IEHDG-IETDG-DEHDG-DQMDG- (SEQ ID NO:4), each of which is followed by a glycine residue, which acts as a stabilizing residue in the N-end rule degradation pathway in yeast (reviewed in Varshavsky, A., *Proc. Natl. Acad. Sci. USA* 93:12142–12149, 1996), and finally, a transcription factor containing the LexA DNA binding domain (Horii, T., et al., *Cell* 23:689–697, 1981). A second construct, designated CLBGG6, was generated that encodes a protein identical to CLBDG6 except that the essential P1 aspartates of the six caspase cleavage sites are replaced with glycines, rendering them nonfunctional.

Construction of Yeast Expression Plasmids.

Plasmids for expression of genes in yeast were derived from the pRS series (Sikorski, R. S., and Hieter, P., *Genetics* 122:19–27, 1989). To express genes in yeast under galactose-inducible control two GAL1 promoter fragments were utilized: a long version, extending from base 1–815, called GALL, and a shorter and somewhat weaker version, extending from base 406–815, called GALS (Johnston, M., and Davis, R. W., *Mol. Cell. Biol.* 4:1440–1448, 1984). The yeast actin terminator, bases 2107–2490 (Genbank accession L00026), was used for all constructs. GALL promoter and actin terminator fragments were inserted into pRS313 (HIS3), pRS314 (TRP1) and pRS315 (LEU2), generating pGALL-(HIS3), pGALL-(TRP1) and pGALL-(LEU2). CLBDG6 and CLBGG6 coding regions were cloned into pGALL-(TRP1). GALS promoter and actin terminator fragments were inserted into pRS315, generating pGALS (LEU2). To express genes under the control of the copper inducible CUP1promoter, a promoter fragment extending from base 1079–1533 of the CUP1 locus (Genbank accession K02204) was utilized. Site-directed mutagenesis was used to mutate the CUP1 promoter to prevent activation in response to glucose starvation (Tamai, K. T., et al., *Mol. Cell. Biol.* 14:8155–8165, 1994). The mutated CUP1 promoter and actin terminator fragments were inserted into pRS315 (LEU2), generating pCUP1-(LEU2).

The coding region for the *C. elegans* caspase CED-3 (Miura, M., et al., *Cell* 75:653-660, 1993) was introduced into pCUP1-(LEU2). Site-directed mutagenesis was used to generate an inactive version of CED-3 in which the active site cysteine was changed to serine (CED-3CS). Full length human caspase 7 (caspase 7FL) (Duan, H. J., et al., *J. Biol. Chem.* 271:1621–1625, 1996), caspase 7 lacking the N-terminal 53 amino acid prodomain (caspase $7^{53}$), and the caspase 8 isoform corresponding to MACHα2 (Boldin, M. P., et al., *Cell* 85:803–815, 1996) or Mch5 (Fernandes-Alnemri, T., et al., *Proc. Natl. Acad. Sci. USA*. 93:7464–7469, 1996) (caspase 8FL), were introduced into pCUP1-(LEU2). Full length DCP1 (Song, Z. W., et al., *Science* 275:536–540, 1997) was introduced into pGALS-(LEU2) and pGALL-(LEU2). Site-directed mutagenesis was used to change the active site cysteine to serine (DCP-ICS). The resulting full length coding region was introduced into pGALL-(LEU2). Full length drICE (Fraser, A. G., and Evan, G. I., *EMBO J.* 16:2805–2813, 1997) was inserted into pGALL-(LEU2). Full length human caspase 9 (Duan, H., et al., *J. Biol. Chem.* 271:16720–16724, 1996; Srinivasula, S. M., et al., *J. Biol. Chem.* 271:27099–27106, 1996) was introduced into pGALL-(LEU2). The region encoding amino acids 1–530 of Apaf-1 (Zou, H., et al., *Cell* 90:405–413, 1997) (Apaf-1$^{530}$) was introduced into pGALL-(HIS3).

Full length DIAP1 (FLDIAP1) and a version of DIAP1 C-terminally truncated following residue 381 (DIAP1BIR) (Hay, B. A., et al., *Cell* 83:1253–1262, 1995) were introduced into pGALL-(HIS3). The mouse IAP MIHA (Uren, A. G., et al., *Proc. Natl. Acad. Sci. USA.* 93:4974–4978, 1996) and baculovirus p35 (Clem, R., et al., *Science* 254:1388–1390, 1991) were introduced into pGALL-(HIS3).

Yeast Transformation and Characterization.

Plasmids were introduced into yeast by lithium acetate transformation. For caspase activity assays in which lacZ expression was monitored, yeast were transformed with pSH18-34 (URA3) (Invitrogen), which carries a LexA-responsive lacZ gene. These cells were then transformed with either pGALL-CLBDG6-(TRP1) or pGALL-CLBGG6-(TRP1). Caspase expression plasmids or an empty expression vector were introduced into these backgrounds and characterized as described below. For caspase activation and inhibition assays, a fourth plasmid was also introduced, either expressing Apaf-1$^{530}$, p35, MIHA, or with no insert. To carry out X-gal filter assays for β-galactosidase (β-gal) activity, transformants were plated on selective plates with glucose (2%) as the sugar source. After three days, duplicate colonies were picked and resuspended in 1 ml of sterile Tris/EDTA, pH 8.0. One μl of each sample was streaked on a minimal medium glucose plate. After two days, a nylon membrane was used to lift the streaked yeast (yeast side upwards) onto a complete medium plate containing 2% galactose and 1% raffinose (gal/raf media) and 3 μM copper sulfate. After various periods of induction the filters were processed for X-gal staining (Breeden, L., and Nasmyth, K., in *Cold Spring Symposia on Quantitative Biology*, Cold Spring Harbor Laboratory, Cold Spring Harbor, N.Y., 50:643–650, 1985). To quantitate β-gal activity, three tubes of liquid selective gal/raf medium were inoculated with single colonies from each transformation plate, grown for 24 hours, then diluted 1:10 into fresh gal/raf selective medium containing the indicated concentration of copper sulfate, and grown for a further 10 hours. ONPG assays were performed as described by Miller (Miller, J. H., in *Experiments in Molecular Genetics*, Cold Spring Harbor Laboratory, Cold Spring Harbor, N.Y., 1972). To assay caspase-dependent cell death and protection by inhibitors, colonies carrying the relevant plasmids were streaked from 2% glucose selective media plates onto gal/raf selective media plates. The plates were photographed after three days.

Expression and Purification of Recombinant *Drosophila* IAPs and Caspases.

The DIAP1 coding region was amplified by PCR using primers that generated an N-terminal myc epitope (EQKLISEEDL) (SEQ ID NO: 1) and introduced into the GST expression vector pGEX4T-1 (Pharmacia). The GST-myc-DIAP1 fusion protein was expressed in *E. coli* strain BL21(DE3)pLysS (Novagen) and affinity purified on glutathione-Sepharose by standard methods. The eluted protein was dialyzed against buffer A [25 mM Tris (pH 8.0), 50 mM NaCl, 10 mM DTT]. Following dialysis, the protein was frozen in aliquots after addition of glycerol to 10%.

DCP-1, initiating at codon 31 (DCP-1$^{31}$), was introduced into pET23a(+) (Novagen), generating a DCP-1$^{31}$-His$_6$ fusion. A similar procedure was used to generate a drICE-His$_6$ fusion protein, in which DrICE initiates at codon 81 (drICE$^{81}$-His6). DCP-1$^{31}$-His$_6$ and drICE$^{81}$-His$_6$ were expressed in the *E. coli* strain BL21(DE3)pLysS. Protein expression and affinity purification from the soluble fraction were carried out using ProBond resin (Invitrogen), by standard methods. Eluted protein was dialyzed against buffer A and subsequently snap frozen in buffer A containing 10% glycerol.

*Drosophila* cDNA Library Construction, and DCP-1 Inhibitor Screening.

*Drosophila* embryonic polyA+ mRNA (Clontech) was converted into cDNA using a Superscript cDNA synthesis kit (GIBCO). cDNAs larger than 600 bp were ligated into a modified version of pGALL-(HIS3) in which the polylinker was expanded to contain XhoI and NotI sites. ElectroMax DH10B cells (GIBCO) were transformed with the ligation mix and used to amplify the library, which contained 5×10$^6$ primary transformants.

W303α yeast carrying pGALL-DCP-1-(LEU2) were transformed with 26 ug of library plasmid DNA, grown in YPD for 3 hrs, washed twice to remove glucose, and plated on gal/raf selective plates. A total of 140,000 transformants were screened. Colonies were picked after 4 days of growth at 30° C. PCR was carried out on DNA isolated from individual colonies using DIAP1 -specific primers.

In Vitro Protease Assays.

DCP-1$^{31}$-His6 and DrICE$^{81}$-His$_6$ caspase activity were measured fluorometrically by following the release of 7-amino-4-trifluoromethyl-coumarin (AFC) from Ac-DEVD-AFC (Enzyme Systems Products) using the finax fluorescence microplate reader (Molecular Devices) with an excitation wavelength of 405 nm and an emission wavelength of 510 nm. The ability of GST-DIAP1 to inhibit caspase activity was determined from caspase activity assay progress curves, in which substrate hydrolysis (100 μM) by DCP-1$^{31}$-His$_6$ (0.2 nM) or drICE$^{81}$-His$_6$ (0.62 nM) was measured in the presence of GST (0.48 μM) or GST-mycDIAP1 (0.16 μM), in caspase activity buffer (50 mM HEPES pH 7.5, 100 mM NaCl, 1 mM EDTA, 0.1% CHAPS, 10% sucrose and 5 mM dithiothreitol).

Example 2

A Reporter for Caspase Activity in Yeast

Site-specific proteolysis plays a critical role in regulating a number of cellular processes. An important class of site-specific proteases are a group of cysteine proteases known as caspases (Alnemri, E. S., et al., *Cell* 87:171, 1996). Extensive genetic and biochemical evidence indicates that caspases play roles as cell death signaling and effector molecules in a number of different contexts, thus making them attractive potential therapeutic targets. Caspases identified to date have been found primarily based on homology to the *C. elegans* caspase CED-3 and mammalian caspase 1, and through biochemical purification (reviewed in Nicholson, D. W. and Thornberry, N., *Trends Biochem. Sci.* 22:299–306, 1997; Salvesen, G. S., and Dixit, V. M., *Cell* 91:443–446, 1997; Thornberry, N. A., and Lazebnik, Y., *Science* 281:1312–1316, 1998; Cryns, V., and Yuan, J., *Genes Dev.* 12:1551–1570, 1998). Viral and cellular activators and inhibitors of caspase function have also been identified in genetic and biochemical screens for regulators of apoptosis (reviewed in Teodoro, J. G., and Branton, P. E., *J. Virol.* 71:1739–1746, 1997; Villa, P., et al. *Trends Biochem.* 22:388–393, 1997; Clem, R. J., and Duckett, C. S., *Trends Biochem.* 7:337–339, 1997). These approaches to isolating caspases and their regulators are limited by the fact that some proteases that cleave a caspase target site and their regulators may not share primary sequence homology with the proteins identified to date, or they may be expressed only in specific tissues with limited availability for biochemical purification. Furthermore, it is clear that caspases regulate processes other than cell death, including cytokine secretion in mammals (Cerretti, D. P., et al., *Science* 256:97–100, 1992; Thornberry, N. A., et al., *Nature* 356:768–774, 1992; Ghayur, T., et al., *Nature* 386:619–623, 1997; Zhang, Y., et al., *J. Biol. Chem.* 273:1144–1149, 1998; Wang, S., et al., *Cell* 92:501–509, 1998) and cell proliferation and oogenesis in *Drosophila* (Song, Z. W., et al., *Science* 275:536–540, 1997; McCall, K., and Steller, H., *Science* 279:230–234, 1998). It seems likely, given the early stage of the field, that more roles exist. Caspases and caspase regulators involved in these processes may be missed in screens that focus strictly on cell death related phenotypes. Thus, molecules that possess caspase or caspase regulatory activity may not have been identified yet. As an alternative approach to identifying novel caspases or caspase regulators it would be useful to have assays for caspase function that are based strictly on protease activity.

Because of the importance of site-specific proteolysis, a versatile system that would was developed to allow the identification of novel site-specific proteases, regulators of the activity of known site-specific proteases, or their substrates. Because caspase cleavage sites have been well defined, and some activators and inhibitors of caspases have been identified, a prototype system was established that would allow positive selection for caspase-like proteases, their activators, and their inhibitors. This approach to identifying these molecules employs reporters for caspase activity that function in living cells. Yeast, though eukaryotic, lacks many of the specialized proteolytic systems found in cells of higher eukaryotes. Thus it constitutes an ideal background in which to carry out function-based screens for these proteases, their regulators and their targets.

Reporters for the activity of specific proteases in bacteria and eukaryotes have been developed using several strategies that involve cleavage-dependent alterations in the activity of specific proteins (McCall, J. O., et al., *Bio/Technology* 12:1012–1016, 1994; Xu, X., et al., *Nucleic Acids Res.* 26:2034–2035, 1998; Sices, J. J., and Kristie, T. M., *Proc. Natl. Acad. Sci. USA* 95:2828–2833, 1998; Struhl, G., and Adachi, A., *Cell* 93:649–660, 1998; Lecourtis, M., and Schweisguth, F., *Current Biol.* 8:771–774, 1998; Stagljar, I., et al., *Proc. Natl. Acad. Sci. USA* 95:5187–5192, 1998). To visualize caspase activity, a fusion protein in which a transcription factor is linked to the intracellular domain of a transmembrane protein by caspase cleavage sites was created. Expression of this protein in yeast, in the presence of an active caspase, results in release of the transcription factor from the membrane, followed by transcriptional activation of a reporter. As described below, this a reporter system, caspase activity can be visualized in yeast, and proteins that act as caspase activators and inhibitors can be identified. Caspase inhibitors can also be identified by virtue of their ability to suppress caspase overexpression-dependent yeast cell death.

In order to monitor caspase activity, in vivo cells were created in which caspase activity stimulates transcriptional activation of a reporter. A fusion protein substrate for caspase cleavage was created in which the transcription factor LexA-B42 (LB) is linked to the truncated cytoplasmic domain of a membrane protein, CD4 (C), by a short linker (DG6) consisting of six different caspase cleavage sites that bracket the specificities of known caspases and the serine protease granzyme B, which cleaves caspases and other targets at sites of similar sequence (See Example 1, Material and Methods, for details). When this molecule, referred to as CLBDG6, is expressed in a reporter strain in which a LexA-dependent promoter drives lacZ expression (LexA/β-gal reporter), levels of β-gal activity should depend on the presence of an active caspase able to cleave one or more of the introduced target sites, thereby releasing LexA-B42 from membrane association. (FIGS. 1A, B).

CLBDG6 was introduced into the LexA/β-gal reporter strain in a plasmid, pGALL-CLBDG6, in which expression is induced in response to galactose. A copper-inducible expression plasmid, pCUP1, containing either no insert or different versions of the caspase CED-3, was introduced into this background. Transformants were initially streaked on glucose medium. Colonies from these streaks were then replica plated onto gal/raf medium containing 3 μM copper to induce expression of CLBDG6, and from the pCUP1 plasmid. After 12 hours of induction, levels of β-gal activity were determined using an X-gal assay in which cells that do not express β-gal remain white, while those that do turn shades of blue.

Figure 1C:
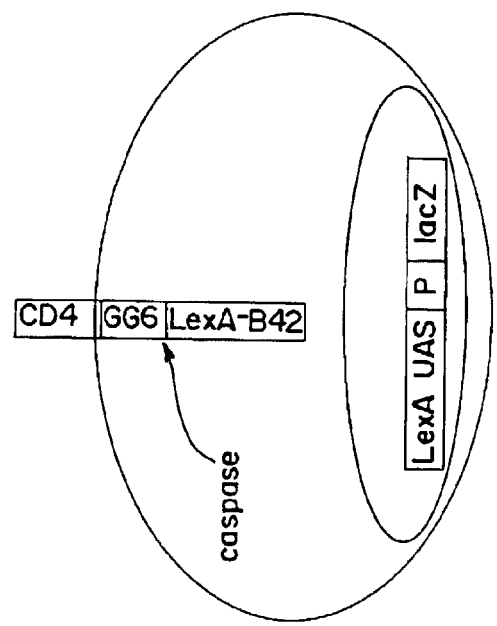
Figure 2:
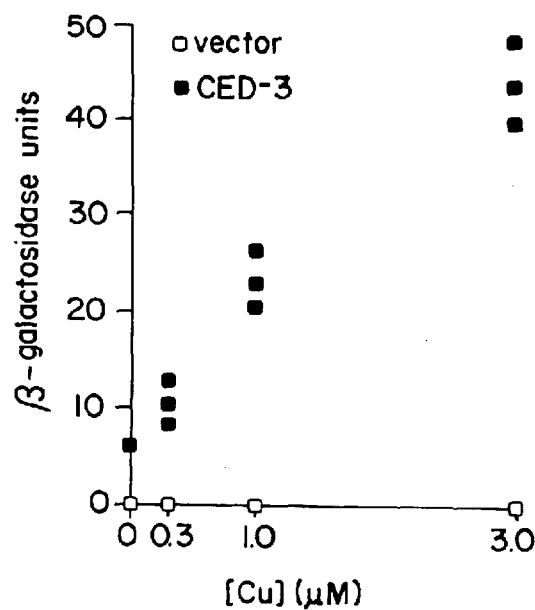
FIG. 2 is a graph of β-galactosidase activity of yeast cells expressing CLBDG6 cultured in differing concentrations of copper demonstrating that these cells act as reporters for CED-3 caspase activity. W303α yeast were transformed with pSH18-34, which carries a LexA-responsive lacZ transcriptional cassette (the LexA/β-gal reporter strain). These cells were transformed with pGALL expression plasmids carrying CLBDG6 (DG6) or CLBGG6 (GG6). These cells also carry a copper-inducible pCUP1 plasmid, which contains either wildtype CED-3 (CED-3), an inactive C to S mutant version of CED-3 (CED-3 C–S), or nothing. Duplicate colonies from each transformation were streaked onto gal/raf medium to induce GAL1-dependent expression of the caspase substrates, and then lifted onto complete media plates with 3 µM copper sulfate to induce caspase expression. After a 12 hour induction an X-gal assay was performed on the filter. Only cells expressing CLBDG6 and wild-type CED-3 have significant α-gal activity. Cultures from three transformants carrying pSH18-34, pGAL-CLBDG6 and either the empty pCUP1 vector or pCUP1-CED-3 were grown to stationary phase, then diluted into medium containing the indicated levels of copper sulfate and grown for a further 10 hrs. ONPG assays were performed and β-gal activity was determined. β-gal activity is shown for the CED-3-expressing cells increased as a function of copper concentration (filled circles, CED-3). It should be noted that no β-gal activity was found in the cultures carrying only the empty pCUP1 vector (open boxes, vector).

Reporter cells that expressed CLBDG6 alone remained white in this assay, indicating that yeast contains negligible amounts of proteases capable of cleaving caspase target sites under standard growth conditions. However, when expression of the *C. elegans* caspase CED-3 (pCUP1-CED-3) was induced, a high level of β-gal activity was observed, which increased in a copper concentration-dependent manner (FIG. 2). Importantly, caspase activity was required for reporter activation, because expression of an inactive CED-3 mutant in which the active site cysteine had been changed to serine (CED-3CS) did not result in β-gal expression. Finally, expression of wildtype CED-3 in a reporter strain in which the essential PI aspartates of the caspase target sites in CLBDG6 had been mutated to glycines (CLBGG6) (FIG. 1C), did not result in β-gal activity, thus the CED-3-dependent induction of β-gal activity was a direct result of cleavage of CLBDG6 at the caspase target sites.

These results establish that yeast can be used as a cell-based reporter system for caspase activity. In order for a caspase to be identified in this assay, the caspase must be active in yeast. Physiological activation of caspases occurs through multiple mechanisms, including recruitment and oligomerization at the plasma membrane, cleavage by caspases or other proteases able to recognize a caspase target site, interactions with members of the CED-4/Apaf-1 family of proteins, and autoactivation. In some cases overexpression alone is sufficient to induce autoactivation, while in other cases significant activation requires interactions with other proteins. Thus it is likely that only proteases in which the primary translation product is active, or in which the protease is able to autoactivate, will be identified in the simplest reporter-based caspase screen. However, more complex screens for caspases that can activate following forced oligomerization or association with potential caspase activators (see Li, P., et al., *Cell* 91:479–489, 1997; Srinivasula, S., et al., *Molecular Cell* 1:949–957, 1998; Yang, X., et al., *Science* 2811355–1357, 1998; Yang, X., et al., *Mol. Cell* 1:319–325, 1998; Muzio, M., et al., *J. Biol. Chem.* 273:2926–2930, 1998) can be produced using the polypeptides of the invention.

Several other caspases were tested in this reporter system. Expression of mammalian caspase $7^{53}$ (below) and full length caspase 8 resulted in reporter-dependent lacZ expression. Expression of human caspase 3, caspase 9 or *Droso-* phila drICE failed to activate reporter expression, even though active forms of these caspases are known to efficiently cleave peptides with the same sequence as the target sites introduced into the CLBDG6 (23, 33). Moreover, although overexpression of wild-type, but not an inactive mutant of CED-3 induced yeast cell death (see below), similar overexpression of caspase 3, caspase 9 or drICE had no effect on cell growth. Based on these observations, it is likely that in yeast the procaspase forms of these caspases do not autoprocess to generate active caspase heterodimers. Caspase 9 is thought to function as an upstream caspase, in which a major mechanism of activation requires association with Apaf-1 (Li, P., et al., Cell 91:479–489, 1997; Srinivasula, S., et al., Molecular Cell 1:949–957, 1998), while caspase-3 is thought to act as a downstream caspase, in which a principal mechanism of activation is cleavage by other caspases (reviewed in Nicholson, D. W. and Thornberry, N., Trends Biochem. Sci. 22:299–306, 1997; Salvesen, G. S., and Dixit, V. M., Cell 91:443–446, 1997; Thornberry, N. A., and Lazebnik, Y. Science 281:1312–1316, 1998; Cryns, V., and Yuan, J., Genes Dev. 12:1551–1570, 1998). drICE activation may be regulated by either of these mechanisms.

Example 3

Activators of Caspase-Dependent Reporter Activation

The fact that certain caspases do not activate in yeast suggests that it should be possible to screen for their activators as molecules that induce reporter expression in the presence of an otherwise inactive caspase. To demonstrate this, an experiment was performed in which caspase activity was monitored in yeast that expressed full length caspase 9, alone or in combination with a fragment of Apaf-1 that is constitutively active with respect to caspase 9 processing activity in vitro (Srinivasula, S., et al., Molecular Cell 1:949–957, 1998). Transformants of the pGALL-CLBDG6 LexA/β-gal reporter strain were generated that carried either two empty vectors, an empty vector and pGALL-Apaf-1$^{530}$, an empty vector and pGALL-caspase 9, or pGALL-caspase 9 and pGALL-Apaf-1$^{530}$. Transformants were initially streaked on glucose medium. Colonies from these streaks were then replica plated onto gal/raf medium to induce GALL-dependent expression. After 16 hrs of induction, levels of β-gal activity were determined using an X-gal assay. Reporter cells that expressed either nothing, caspase 9, or Apaf-1$^{530}$ alone remained white in this assay, indicating that caspase activity was not induced. However, colonies that expressed both caspase 9 and Apaf-1$^{530}$ showed robust β-gal activity, suggesting the occurrence of Apaf-1$^{530}$-mediated activation of the otherwise inactive procaspase 9.

β-gal activity, as assayed following replica plating of colonies, was chosen as the basis for the caspase reporter assay because caspases are conditionally expressed following replica plating. Thus, their identification is feasible even if their expression is toxic to cells. However, caspase activity screens can also be adapted to positive, survival-based screening assays by requiring LexA-dependent expression of a yeast auxotrophic marker such as HIS3 or URA3. False positives in these caspase reporter assays could arise because introduced proteins bind to the LexA binding sites and activate transcription directly, or because they encode proteases that cleave CLBDG6, but not at the caspase target sites. Both classes of false positives can be identified by the fact that they should still activate lacZ expression when introduced into a LexA/β-gal reporter strain that expresses CLBGG6, the false positive reporter strain (FIG. 1C).

Example 4

Suppression of Caspase-Dependent Reporter Activation by Caspase Inhibitors

Figure 1D:
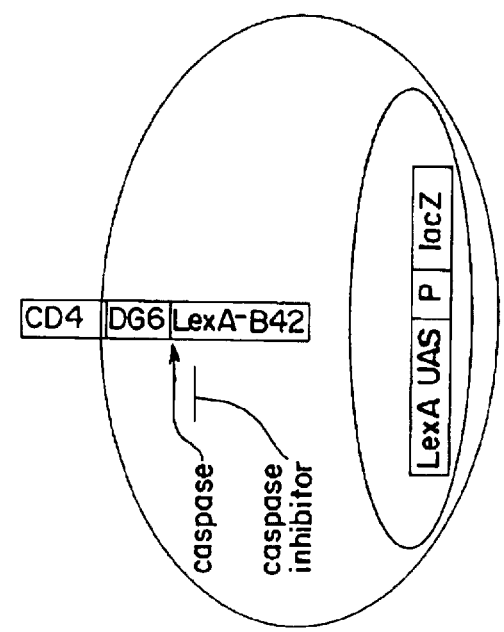
Figure 1A:
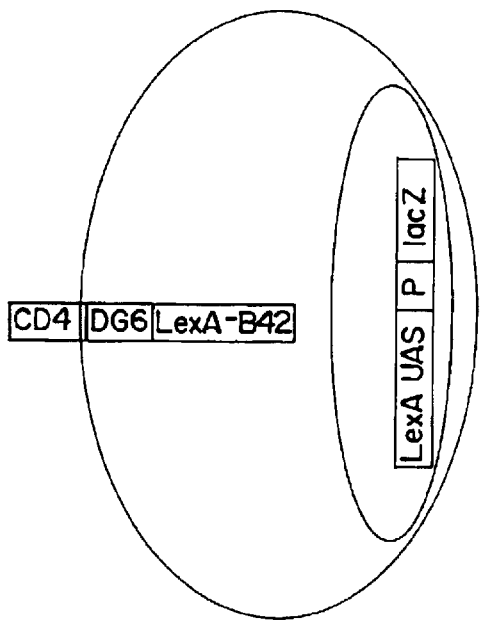
Figure 3A:
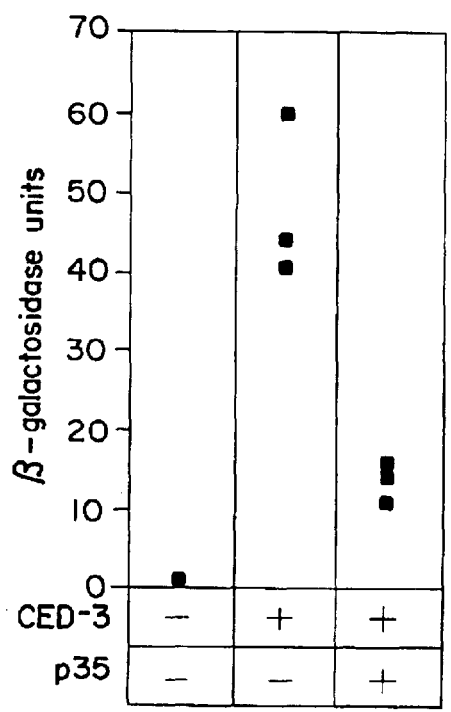
FIG. 3A is a plot of the results obtained from cultures of caspase transformants, and documents significant β-gal activity, which was suppressed by GALL-dependent expression of baculovirus p35.
Figure 3B:
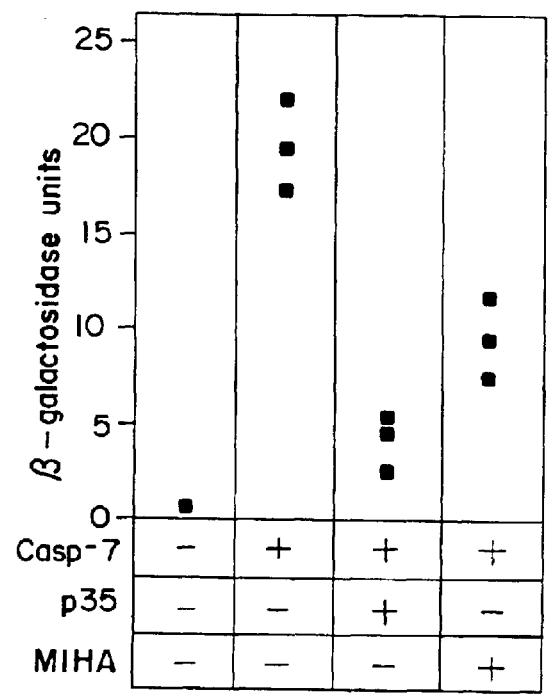
FIG. 3B is a plot of the results obtained in an similar experiment: expression of caspase $7^{53}$ was induced in cells that express baculovirus p35 or the mouse IAP MIHA. Expression of caspase $7^{53}$ resulted in a significant increase in cellular β-gal activity, which was suppressed by GALL-dependent expression of p35 or MIHA.

Once a reporter for the activity of a specific caspase has been established in yeast, it should be possible to screen for inhibitors of that activity by identifying cells that express the protease, but in which reporter activity is repressed (FIG. 1D). The feasibility of this approach was demonstrated by showing that two different families of caspase inhibitors, exemplified by baculovirus p35, and the murine IAP MIHA, suppress caspase-dependent reporter activation.

p35 is a broad specificity caspase inhibitor in which inhibition is associated with cleavage (reviewed in Teodoro, J. G., and Branton, P. E., J. Virol. 71:1739–1746, 1997). The IAPs comprise a second class of caspase inhibitors distinct from p35, in which cleavage of the inhibitor does not play a role. IAPs were originally identified in the baculovirus system by virtue of their ability to substitute for baculovirus p35 as suppressors of viral infection-induced cell death (Crook, N. E., et al., J. Virol. 67:2168–2174, 1993). IAP homologs have now been found in other viruses, Drosophila, C. elegans, mammals and yeast, and are characterized by one or more N-terminal repeats known as baculovirus IAP repeats (BIRs). Many also have a C-terminal RING finger motif (reviewed in Teodoro, J. G., and Branton, P. E., J. Virol. 71:1739–1746, 1997; Villa, P., et al. Trends Biochem. 22:388–393, 1997; Clem, R. J., and Duckett, C. S., Trends Biochem. 7:337–339, 1997; Uren, A. G., et al., Trends Biochem. Sci. 23:159–162, 1998). Several mammalian IAPs: XIAP, cIAP1, and cIAP2, bind to and directly inhibit caspases –3 and –7 in vitro (Deveraux, Q. L., et al., Nature, 388:300–304, 1997; Roy, N., et al., EMBO J. 16:6914–6925, 1997). pGALL-CLBDG6 and either an empty pCUP1 plasmid or a pCUP plasmid containing CED-3 or caspase 7$^{53}$ was introduced into the LexA/β-gal reporter strain along with either an empty pGALL expression vector, a pGALL expression vector carrying p35, or a pGALL expression vector carrying MIHA (murine XIAP). Transformants were grown in galactose-containing medium to induce expression of CLBDG6 and the caspase inhibitor, and then transferred to medium containing galactose and 3 μM copper, to induce expression of the caspase. β-gal activity was determined following a 10 hr copper induction. As shown in FIG. 3 (FIG. 3A and FIG. 3B), expression of p35 inhibited both CED-3 and caspase 7$^{53}$ activity roughly fivefold. A similar, though somewhat weaker (approximately twofold) inhibition of caspase 7$^{53}$ activity was seen in the presence of MIHA (FIG. 4B), indicating that caspase-IAP interactions can be detected in this assay.

Example 5

Caspase Overexpression-Dependent Yeast Cell Death and the Suppression of this Cell Death by Caspase Inhibitors In the above assay, the presence of a caspase inhibitor is indicated by a decrease in β-gal activity. However, in many situations it would be useful if caspase inhibition was coupled to a positive reporter output. A direct approach to identifying caspase inhibitors rests on the observation that high level expression of active caspase causes yeast cell death. Low level expression of the Drosophila caspase DCP-1 from the induced CUP-1 promoter did not significantly compromise yeast cell growth. Higher level expression from the GAL promoter, however, did result in cell lethality. Cells were able to grow on galactose-containing media if they carried an empty pGALL expression vector, but not if they carried a pGALL-DCP-1 expression construct. This effect of DCP-1 expression was due to cell death since a greater than 250-fold decrease in the number of colony forming units was seen when cells carrying the pGALL-DCP-1 expression plasmid were grown for 12 hours in liquid gal/raf medium, thus inducing high level DCP-1 expression, and then plated on glucose-containing medium. Importantly, GALL-DCP-1-expression-dependent cell killing depended on caspase activity because expression of an inactive mutant form of DCP-1 (DCP-1 C285S) did not cause cell death. Caspase-mediated cell death in yeast may be a general phenomenon because other caspases that are active in yeast, including full length CED-3, full length caspase 8, and caspase $7^{53}$, block colony formation when expressed under control of the strong GALL promoter.

To demonstrate that caspase inhibitors can be identified as proteins that restore cell viability to yeast expressing an active caspase, an experiment was carried out in which the broad specificity caspase inhibitor p35 was coexpressed with full length DCP-1. We introduced pGALL expression plasmids that either had no insert, or that carried p35, into cells carrying a pGALS-DCP-1 plasmid. Cells from colonies carrying these plasmids were grown on glucose-containing media and then streaked onto gal/raf media to induce expression of the caspase and the potential inhibitor. pGALS-dependent expression of DCP-1 in the presence of an empty pGALL expression vector resulted in no cell growth. In contrast, coexpression of baculovirus p35 with DCP-1 resulted in a dramatic rescue of cell growth.

Figure 4A:
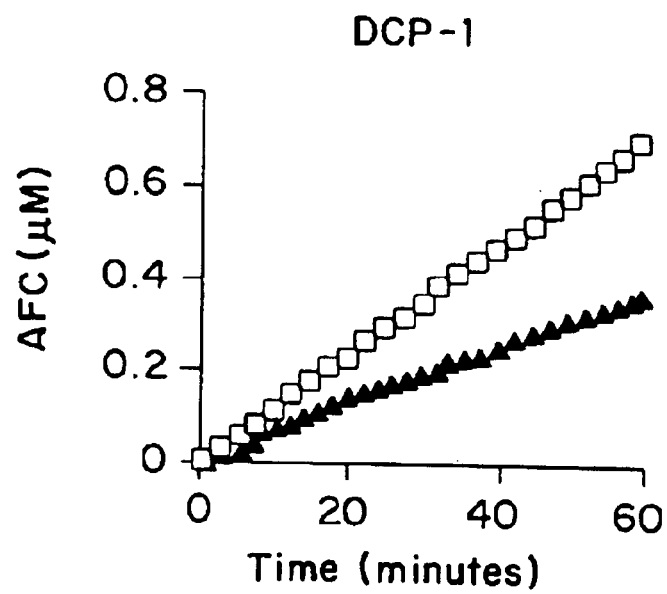
FIG. 4A demonstrates that GST-DIAP1 inhibits the caspase activity of bacterially synthesized DCP-1, but not drICE. Purified GST-DIAP1 (0.16 µM) (open triangles) or GST (0.48 µM) (open squares) was incubated with a fixed amount of DCP-$1^{31}$His$_6$ (0.2 nM) in caspase activity assay buffer containing 100 µM of the Ac-DEVD-AFC substrate. Release of was monitored fluorometrically over time. GST-DIAP1 inhibits DCP-1-dependent caspase activity.
Figure 4B:
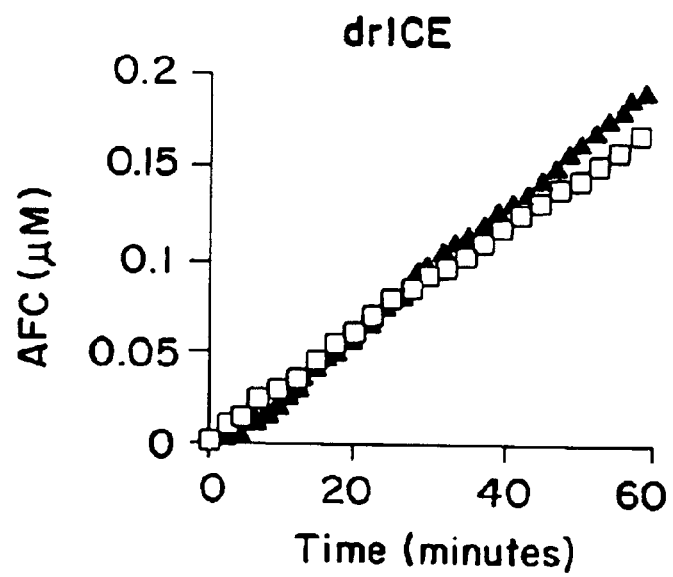
FIG. 4B is a plot of the results obtained in similar experiments in which 0.62 nM drICE$^{81}$His$_6$ was incubated in caspase activity buffer with GST (0.48 µM), or GST-DIAP1, (0.16 µM). No inhibition of drICE activity by GST-DIAP1 was seen.

To determine if a yeast survival-based screen can be used to identify novel caspase inhibitors, we transformed yeast carrying pGALS-DCP-1 with a *Drosophila* pGALL embryonic cDNA expression library and plated these cells on gal/raf medium. In a screen of about $1.4 \times 10^5$ transformants approximately 50 positives were obtained. These were tested by PCR and all found to correspond to DIAP1, which was originally identified as an inhibitor of reaper or hid overexpression-induced, caspase-dependent cell death in the fly eye (Hay, B. A., et al., *Cell* 83:1253–1262, 1995). In the fly eye, and in cell culture (Harvey, A. J., et al., *Cell Death Differ.* 4:733–744, 1997; Vucic, D., et al., *Proc. Natl. Acad. Sci. USA* 94:10183–10188, 1997; Vucic, D., et al., *Mol. Cell. Biol.* 17:667–676, 1998; Hawkins, C. J., et al., *Cell Death Differ.* 5:569–576, 1998), it was also found that cell death could be suppressed by expression of an N-terminal DIAP1 fragment containing the two BIR repeats, but lacking the C-terminal RING finger domain. To determine if the same fragment of DIAP1 was sufficient to block DCP-1-dependent cell killing in yeast, an experiment was carried out in which full length DIAP1, an N-terminal fragment of DIAP1, or an empty vector, was expressed under GALL control, in the presence of GALS-driven DCP-1. Inhibition of DCP-1-dependent cell death was seen when DIAP1 or the N-terminal fragment of DIAP1 containing only the DIAP1 BIR repeats was coexpressed with DCP-1. To determine if the observed interaction between DIAP1 and DCP-1 was direct, bacterially synthesized GST-DIAP1 was generated, as well as $His_6$ tagged versions of prodomainless DCP-1 ($DCP-1^{31}$-$His_6$) and drICE ($drICE^{81}$-$His_6$). As shown in FIG. 4, GST-DIAP1 inhibited $DCP-1^{31}$-$His_6$ caspase activity, but had little, if any effect on that of $drICE^{81}$-$His_6$. Thus, these results demonstrate that caspase inhibitors can be identified as molecules that block GAL-driven, caspase-dependent cell death.

Thus a cell-based assay has been developed for the activity of one group of proteases, the caspases, in which caspase activity is monitored either by the cleavage-dependent release of a transcription factor from its transmembrane anchor and subsequent activation of a reporter, or by induction of cell killing. Both reporter activation and cell killing are suppressed by known caspase inhibitors. This system has been used to directly isolate caspase inhibitors from a *Drosophila* embryo cDNA library.

Yeast carrying the transcription-based caspase reporter should be useful as a background in which to carry out screens for proteins that cleave a caspase target site and for their regulators. Because yeast can be transformed with high efficiency, it also constitutes an ideal system in which to carry out large scale mutagenesis studies of particular proteases or their regulators. It may also be possible to screen for cellular targets of specific caspases by using artificial substrate libraries in which cDNA fragments substitute for the caspase target site linker in the caspase substrate fusion protein CLBDG6. A transcription-based reporter strategy similar to that described here may also provide a way to monitor caspase activity in cells of higher eukaryotes. Finally, substituting caspase cleavage sites for those of other site-specific proteases in the CLBDG6 reporter will enable the identification and study of these proteins and their regulators.

Although the invention has been described with reference to the presently preferred embodiment, it should be understood that various modifications can be made without departing from the spirit of the invention. Accordingly, the invention is limited only by the following claims.

What is claimed is:

1. A fusion protein comprising:

a) a reporter polypeptide comprising a C-terminal Lex A-B42 transcription factor linked to a linker polypeptide comprising a protease cleavage site; and b) a repressor polypeptide comprising an N-terminal fragment of CD4 that represses transcriptional activity of the reporter polypeptide by conferring a specific localization in a cell such that the reporter polypeptide has reduced transcriptional activity, wherein said repressor polypeptide is linked to the linker polypeptide, and wherein, upon cleavage of said linker polypeptide at said protease cleavage site, an increase in the transcriptional activity of said reporter polypeptide can be detected.

2. The fusion protein of claim 1, wherein said protease cleavage site is a caspase cleavage site.

3. A fusion protein comprising:

a) a reporter polypeptide comprising a C-terminal Lex A-B42 transcription factor linked to a linker polypeptide comprising a protease cleavage site; and b) a repressor polypeptide comprising an N-terminal fragment of CD4 or an amyloid precursor protein that represses transcriptional activity of the reporter polypeptide by conferring a specific localization in a cell such that the reporter polypeptide has reduced tscriptional activity, wherein said repressor polypeptide is linked to the linker polypeptide, and wherein, upon cleavage of said linker polypeptide at said protease cleavage site, an increase in the transcriptional activity of said reporter polypeptide can be detected.

4. The fusion protein of claim 3, wherein said protease cleavage site is a caspase cleavage site.

* * * * *

UNITED STATES PATENT AND TRADEMARK OFFICE
CERTIFICATE OF CORRECTION

PATENT NO. : 6,884,870 B2
DATED : April 26, 2005
INVENTOR(S) : Hay and Hawkins

It is certified that error appears in the above-identified patent and that said Letters Patent is hereby corrected as shown below:

Title page,
Item [12], United States Patent, delete "Bruce A. Hav" and replace with
-- Bruce A. Hay --
Item [75], Inventors, delete "Bruce A. Hav" and replace with
-- Bruce A. Hay --

Signed and Sealed this

Twelfth Day of July, 2005

JON W. DUDAS
*Director of the United States Patent and Trademark Office*